US011596390B1

(12) United States Patent
Nibhanipudi

(10) Patent No.: US 11,596,390 B1
(45) Date of Patent: Mar. 7, 2023

(54) METHOD OF TEMPORAL DETERMINATION OF SEMEN-BASED DNA SAMPLE

(71) Applicant: Kumara V. Nibhanipudi, Scarsdale, NY (US)

(72) Inventor: Kumara V. Nibhanipudi, Scarsdale, NY (US)

(*) Notice: Subject to any disclaimer, the term of this patent is extended or adjusted under 35 U.S.C. 154(b) by 0 days.

(21) Appl. No.: 17/729,907

(22) Filed: Apr. 26, 2022

(51) Int. Cl.
*A61B 10/00* (2006.01)
*C12Q 1/6806* (2018.01)

(52) U.S. Cl.
CPC ...... *A61B 10/0058* (2013.01); *A61B 10/0096* (2013.01); *C12Q 1/6806* (2013.01)

(58) Field of Classification Search
CPC ............ A61B 10/0058; A61B 10/0096; A61B 10/045; A61B 10/0291; A61B 2010/0074; A61B 2010/2016; C12Q 1/6806
See application file for complete search history.

(56) References Cited

U.S. PATENT DOCUMENTS 8,734,364 B1 * 5/2014 Mantzaris .......... A61B 10/0291
600/572
9,730,679 B1 * 8/2017 Cover ................ A61B 10/0291

OTHER PUBLICATIONS

"Adult and Child Sexual Assault Protocols. Apr. 2015. Office of the Attorney General of Florida. pp. 17-21" (Year: 2015).*
"National Best Practices for Sexual Assault Kits. Aug. 2017. National Institute of Justice. p. 21" (Year: 2017).*
"Apostolov, Aleksandar. Differentiation of mixed biological traces in sexual assaults using DNA fragment analysis. Mar. 2014. Biotechnology, Biotechnological Equipment. pp. 301-305" (Year: 2014).*
"Nittis, M. Sexual Assault Examination (Clinical Forensic Medicine). 2020. Springer. Fourth Edition. pp. 112-116" (Year: 2020).*

* cited by examiner

*Primary Examiner* — Nathan J Jenness
*Assistant Examiner* — Severo Antonio P Lopez
(74) *Attorney, Agent, or Firm* — MaxGo Law PLLC

(57) ABSTRACT

A method and corresponding test kit is provided for the determination of whether a non-consensual sexual encounter between known individuals has occurred when previous consensual relations have taken place between the known individuals.

10 Claims, 3 Drawing Sheets

METHOD OF TEMPORAL DETERMINATION OF SEMEN-BASED DNA SAMPLE

FIELD OF THE INVENTION

The present invention in general relates to the field of forensics and in particular to a method of temporal determination of semen-based samples recovered from a vaginal canal.

BACKGROUND OF THE INVENTION

Cases of sexual abuse and rape are often carried out by a perpetrator known to a victim. Random acts of sexual violence by unknown perpetrators are much less common. It is also often the case that there have been multiple experiences among the known partners and there is an allegation that the last encounter was non-consensual. While most of the time the incidences happen with bilateral verbal consent, sexual encounters amongst known partners can become sexual abuse or rape if one partner does not give consent or worst of all a sexual act is forced on the unwilling partner.

In instances where the victim's assailant is known to them and they previously had consensual sexual experiences in the two days prior to a non-consensual encounter, it is difficult to prosecute the offense as the perpetrator offers a defense that the event never occurred or if admitted, that the encounter was consensual. If the victim that files criminal charges is female, she will be subjected to a physical pelvic exam to collect forensic physical evidence as well as cultures, semen collection, and finally a specimen for DNA analysis.

However, conventional DNA based testing of collected semen from a woman is unable to provide a date of when an incident occurred. It is currently not possible to establish the date of a non-consensual sexual encounter relative to consensual sexual activity based on DNA evidence. The collection of evidence of non-consensual sexual activity is further complicated if the victim showers or otherwise attempts to cleanse themselves.

Thus, there exists a need for an improved diagnostic method to determine the timing of a non-consensual sexual encounter has occurred relative to previous consensual relations between the same individuals.

SUMMARY OF THE INVENTION

A diagnostic method is provided for obtaining temporal semen samples. The method includes semen DNA collection from vaginal canal regions that correspond to a proximal region corresponding to an entry point the woman's vaginal canal, a middle region, and a distal region. By providing three individual swabs that each target one of the three regions, one obtains individual samples from each of the corresponding proximal region, middle region, and the distal region. Subsequently, the three individual swabs are tested to determine whether the semen collected differs between the three regions of the woman's vaginal canal.

A kit is provided for obtaining temporal semen samples. The kit includes a measuring device, three testing swabs, three vials for individually holding each of the three testing swabs; and a set of labels with matching indicia.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains the preferred embodiments of the invention, together with advantages and features, by way of example with reference to the drawings.

DESCRIPTION OF THE INVENTION

The present invention has utility as an improved diagnostic method and corresponding test kit for the determination of whether a non-consensual sexual encounter between known individuals has occurred, when previous consensual relations have taken place between the known individuals based on temporal changes in the samples so collected.

Embodiments are beneficial for use in cases where two heterosexual partners are in an intimate relationship with multiple sexual encounters, and the last consensual encounter being two days prior to a non-consensual sexual encounter. The victim identification taken for collection of forensic evidence on the same day of reporting or filing a complaint. It is noted that the victim cleansing her pelvic region is invariably destructive of evidence. Added to this, as noted above conventional DNA evidence is not determinative the date of encounter. However, embodiments of the present invention take advantage of the observation that semen is deposited in whole vagina canal, and that cleansing will not totally remove evidence therefrom. Crusting of semen within the vaginal canal will take a few days as compared to a liquid consistency on day one relative to the offense. The specimen collected from the crusty seminal material deposited on walls deep inside the vaginal canal may accurately predict past occurrence of sexual activity rather than on day one, as the older semen has begun to dry and form the crust.

The temporal relationship between positional depth and differences in consistency of the deposited semen in the vaginal canal is used to determine a timeline of sexual encounters.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Figure 1:
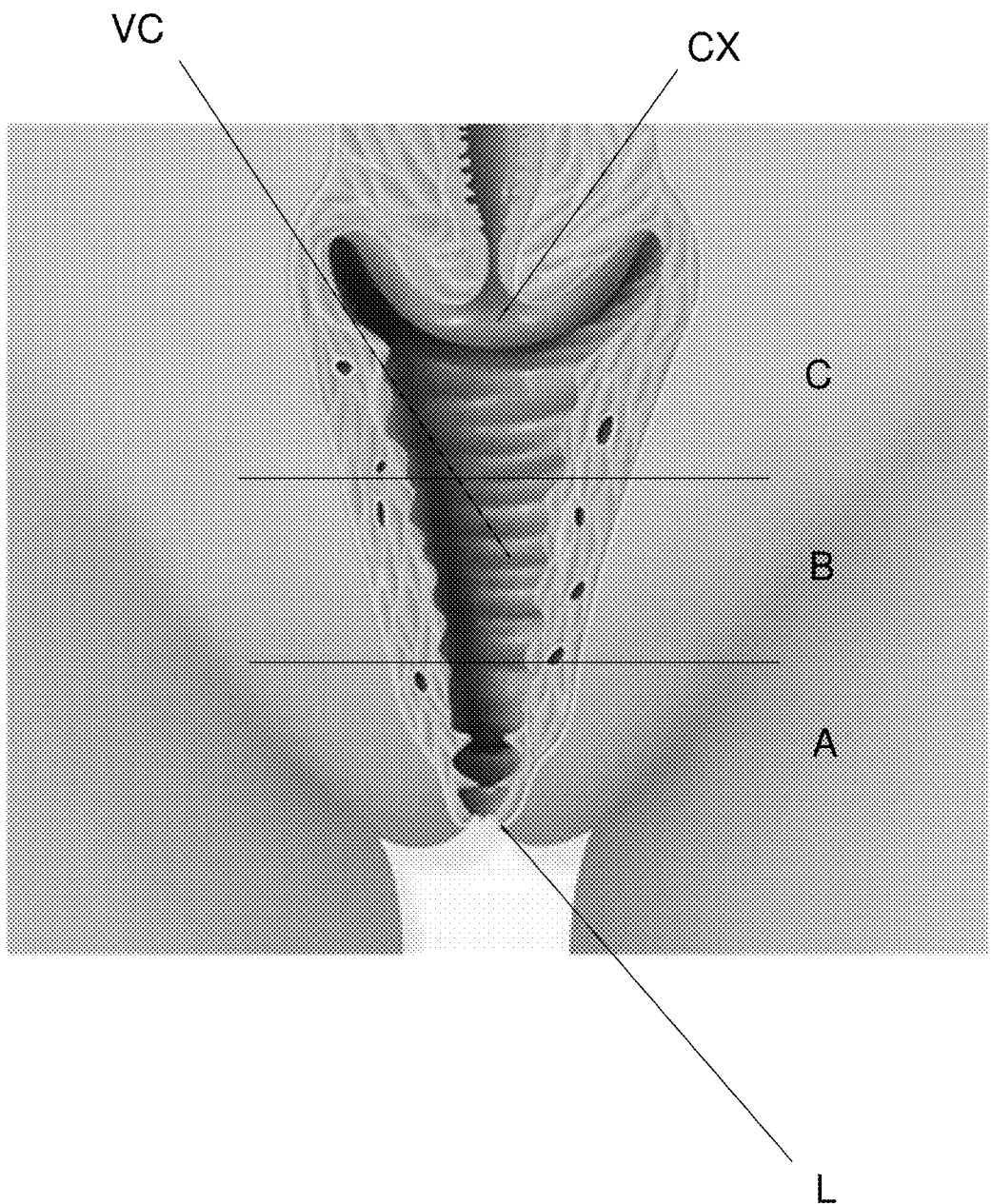
FIG. 1 is a cutaway representation of a female pelvic region that illustrates the vaginal canal divided into three regions (proximal, middle, distal) from the labial opening to the cervix.

Referring now to the figures, FIG. 1 is a cutaway representation of a female pelvic region that illustrates the vaginal canal, VC divided into three regions (proximal, middle, distal) from the labial opening L to the cervix CX, where the three regions are indicated as A, B, and C, respectively. It is appreciated that more than three regions are designated for collection of samples without departing from the spirit of the present invention. The average depth of a vaginal canal is 9.6 centimeters (3.78 inches). Jillian Lloyd et al., *Female genital appearance: 'normality' unfolds*, BJOG An International Journal of Obstetrics and Gynaecology, Royal College of Obstetricians and Gynaecologists, 2005). This finding is subject to recognition that the vaginal canal has the ability to stretch.

In embodiments of the present invention for collection purposes during a pelvic examination, the length of the vagina is divided into the three or more regions as shown in FIG. 1, a first third (⅓rd) as a proximal region, a middle third (⅓$^{rd}$) as a middle region, and lastly a deeper third (⅓rd) portion as a distal region. In order to obtain and to identify where a sample was obtained three swabs of varying lengths that correspond to the vaginal depth of each region are named as follows: a first proximal swab, a second middle swab, and a third distal swab for the deeper ⅓rd portion. In most situations, the semen found in the distal upper region of the vaginal canal has the longest deposition time and becomes a dried crusty deposit on the walls of vagina. Therefore, the third distal swab that is intended for deeper collection should definitely scrap the walls so that the semen collected will be that of previous occurrences of sexual relations rather than from the present encounter that was presumably not consensual.

Figure 2:
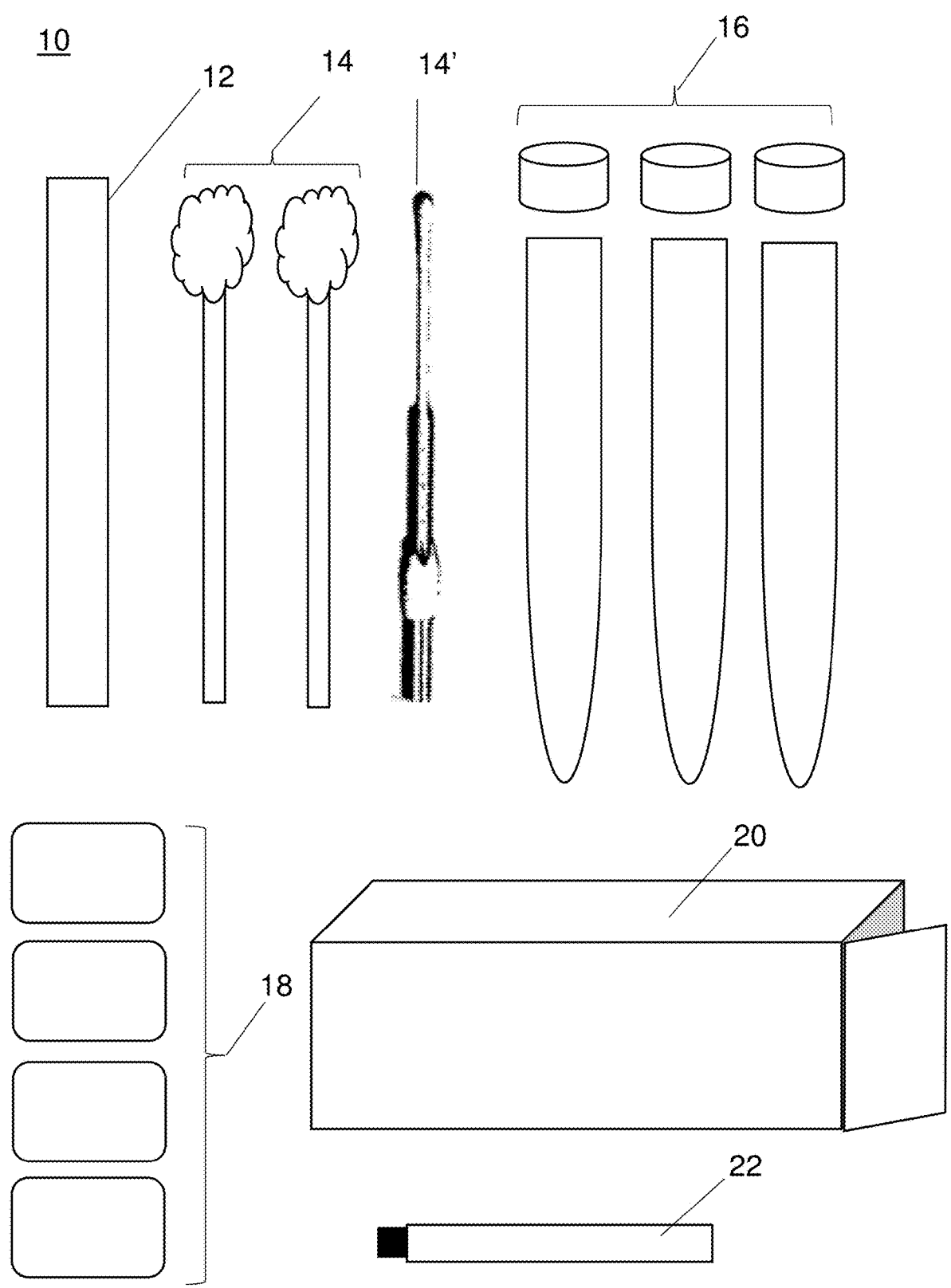
FIG. 2 illustrates a testing kit for carrying out a method for temporal seminal collection in accordance with embodiments of the invention.

FIG. 2 illustrates a testing kit 10 for carrying out a method for temporal seminal collection in accordance with embodiments of the invention. Embodiments of the testing kit 10 include a measuring device or ruler 12 to measure the length of the vaginal canal at the time of the examination, three testing swabs that are all of the types shown at 14, 14' or a combination thereof are provided. It is appreciated that a sheathed swab facilitates sample collection without risk of incidental sample collection as the swab is retracted from the vaginal canal. The swabs are either cut or marked into three lengths based on the measured total length of the vaginal canal and the establishing of the three regions in the vaginal canal. A set of vials 16 for storing the testing swabs following sample acquisition. The set of vials 16 may each be treated with a chemical preservative to maintain the viability of the sample. A set of labels 18 with matching indicia may be provided to label the three vials 16 and the storage or shipping box 20. The labels 18 may be barcodes or color coded. The indicia 18 may be non-identifying to preserve confidentiality of the samples. The storage or shipping box 20 may then be brought to an onsite lab or sent to a separate testing facility. A marker 22 may also be provided in embodiments of the testing kit.

Figure 3:
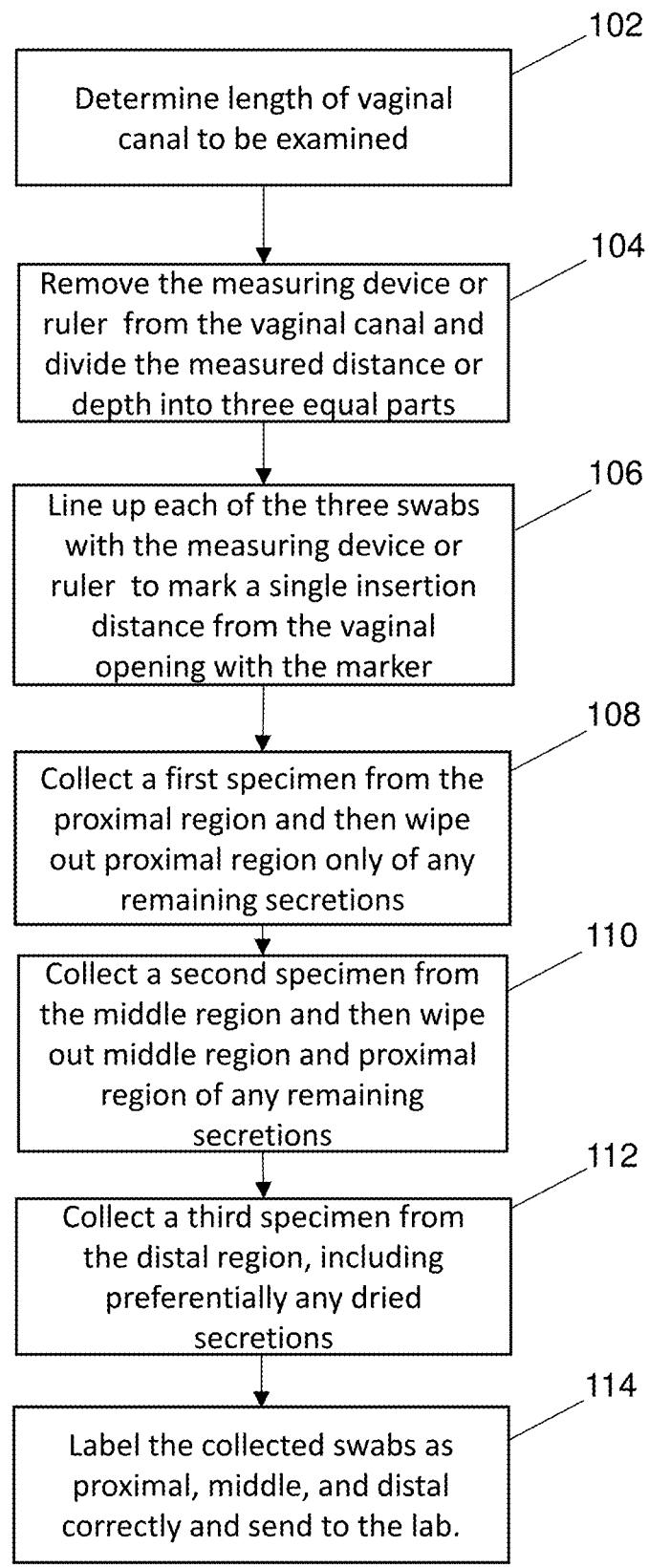
FIG. 3 is a flowchart representation of the temporal method of seminal collection in accordance with embodiments of the invention.

FIG. 3 is a flowchart representation of an embodiment the temporal method 100 of seminal collection from a vaginal canal. The method starts by introducing a sterile plastic measuring device or ruler 12 into the vaginal canal to determine the depth or length of vaginal canal to be examined (Step 102). Remove the measuring device or ruler 12 from the vaginal canal and divide the measured distance or depth into three equal parts that represent a proximal, medial, and distal region of the vaginal canal by imprinting on the scale with marker pen two dividing lines to demarcate the three regions of the vaginal canal (Step 104). Line up each of the three swabs 14 with the measuring device or ruler 12 to mark each of the swabs 14 with a single insertion distance from the vaginal opening with the marker 22, so as to indicate one of proximal, medial, and distal to approximate the required wipe area in each region to collect a specimen using the marked guidance (Step 106). Collect a first specimen for the proximal region and then wiping out the proximal region only of any remaining secretions (Step 108). Introduce the middle swab and after collecting material from the middle region, wiping out both the proximal and middle portions (Step 110). Introduce the distal swab into distal region and swab the roof (i.e., cervix) of the distal portion, as well as the sides. Collect preferentially any dried secretions (Step 112). Label the collected swabs as proximal, medial, and distal and send to the lab for DNA analysis (Step 114). As previously noted, the DNA evidence collected using the aforementioned three swab method may provide an idea of the relative date of a sexual encounter, especially prior occurrences as prior deposited semen will be crusted and stick to vaginal walls.

If semen DNA samples collected is present in all three regions namely proximal, middle and distal regions of the vaginal canal as measured as approximate thirds thereof, it is not possible to predict the date of sexual encounter as to whether consensual or forced. In this case, the semen DNA evidence collected by the present invention is less than determinative deciding if the legal definition of rape or sexual assault has been met to prosecute. If semen DNA samples collected are present only in the proximal and middle regions and more so in proximal regions of the vaginal canal, and semen DNA not present in distal third thereof, the present invention is strongly suggestive of that the sexual encounter was within 2 days and is strongly suggestive of a forced sexual encounter for legal prosecution purposes.

EXAMPLES

Example 1

A sexually active woman accuses a man of unwanted sexual intercourse. The woman reports the unwanted sexual encounter to the police. The woman undergoes the three-swab method to confirm that the semen from latest sexual encounter belongs to the man she is accusing, as the semen belongs to the accused man is found in the proximal region and differs from semen found in the distal region.

Example 2

A sexually active woman has multiple sexual encounters with a man, and then wishes to stop the activity, but the man forces sexual intercourse on the non-consenting women. The woman accuses the man of unwanted sexual intercourse. The woman reports the unwanted sexual encounter to the police. The woman undergoes the three-swab method to confirm that the semen from latest sexual encounter belongs to the man she is accusing, as the semen belongs to the accused man is found in the proximal region, as well as from older semen found in the distal region.

The foregoing description is illustrative of particular embodiments of the invention but is not meant to be a limitation upon the practice thereof. The following claims, including all equivalents thereof, are intended to define the scope of the invention.

The invention claimed is:

1. A method for obtaining temporal semen samples as evidence of a forced sexual encounter having occurred within two days of a previous consensual encounter,
said method comprising:
providing three or more individual swabs that each target one of three or more regions of a subject vaginal canal to obtain separate individual semen samples with each of the three or more individual swabs that directly correspond to one or the three or more regions of the vaginal canal; and
providing the three or more individual swabs to test whether the separate individual semen samples collected differ between the three or more regions of the vaginal canal, where a temporal relationship between positional depth of the separate individual semen samples and differences in consistency of deposited semen in the vaginal canal is used to determine a timeline of sexual encounters.

2. The method of claim 1 further comprising measuring the length of the vaginal canal by inserting a measuring device.

3. The method of claim 2 further comprising dividing the measured length on the measuring device into three lengths that correspond to a proximal region, a middle region, and a distal region of the vaginal canal.

4. The method of claim 3 further comprising lining up each of the three or more individual swabs to mark each swab with a single insertion distance from an opening of the vaginal canal that corresponds to one of corresponding regions of the proximal region, the middle region, and the distal region of the vaginal canal.

5. The method of claim 4 further comprising introducing a first swab of the marked three or more individual swabs into the vagina canal and collecting a first specimen for the proximal region and subsequently wiping out the proximal region only of any remaining secretions.

6. The method of claim 5 further comprising introducing a second swab of the marked three or more individual swabs into the vaginal canal and after collecting a second specimen from the middle region, wiping out both the proximal and the middle regions.

7. The method of claim 6 further comprising introducing a third swab of the marked three or more individual swabs into the vaginal canal and collecting a third specimen from the distal region.

8. The method of claim 7 wherein the collecting the third specimen further comprises swabbing a roof (i.e., cervix) of the distal portion, as well as sides of the vaginal canal in the distal region to target the collection of any dried semen.

9. The method of claim 1 wherein at least one of the three or more individual swabs is a sheathed swab.

10. The method of claim 1 further comprising labelling each of the three or more individual swabs as to which of the three or more regions of the vaginal canal the swab is targeted to sample.

* * * * *